United States Patent [19]

Carll

[11] Patent Number: 4,786,875

[45] Date of Patent: Nov. 22, 1988

[54] CONDUCTIVITY MEASURING CIRCUIT

[75] Inventor: Kenneth B. Carll, Bridgeton, N.J.

[73] Assignee: General Signal Corporation, Stamford, Conn.

[21] Appl. No.: 889,033

[22] Filed: Jul. 22, 1986

[51] Int. Cl.⁴ .................. G01N 27/42; G01N 27/02
[52] U.S. Cl. .................. 324/444; 324/443; 324/65 R
[58] Field of Search .................. 324/439–444, 324/62 R, 64 R, 65 R; 204/406, 400

[56] References Cited

U.S. PATENT DOCUMENTS

| | | |
|---|---|---|
| 3,170,111 | 2/1965 | Case . |
| 3,493,857 | 2/1970 | Silverman .................. 324/442 |
| 3,495,164 | 2/1970 | Dauphinee . |
| 3,582,767 | 6/1971 | Brum .................. 324/442 |
| 3,665,302 | 5/1972 | Lees .................. 324/64 |
| 3,757,205 | 9/1973 | Dauphinee .................. 324/444 |
| 3,946,309 | 3/1976 | Roughton .................. 324/64 |
| 3,965,414 | 6/1976 | Teass . |
| 4,028,618 | 3/1980 | Teass . |
| 4,181,880 | 6/1977 | Teass . |
| 4,303,887 | 12/1981 | Hill .................. 324/441 |
| 4,323,972 | 4/1982 | Winter . |
| 4,331,923 | 5/1982 | Akers . |
| 4,383,221 | 5/1983 | Morey .................. 324/439 |
| 4,618,818 | 10/1986 | Horn .................. 324/62 R |
| 4,652,830 | 3/1987 | Brown .................. 324/439 |
| 4,656,427 | 4/1987 | Dauphinee .................. 324/443 |
| 4,682,113 | 7/1987 | Barben .................. 324/441 |

FOREIGN PATENT DOCUMENTS 1623034 3/1975 Fed. Rep. of Germany .

Primary Examiner—Reinhard J. Eisenzopf
Assistant Examiner—Jose M. Solis
Attorney, Agent, or Firm—William G. Miller, Jr.; Harold Huberfeld

[57] ABSTRACT

A circuit for measuring the conductivity of a solution by applying a known ac current source across a pair of electrodes in the solution and utilizing an analog-to-digital dual slope converter, such as those of the integrated circuit type which include capacitor sampling of the signal input, for conversion of the ac voltage drop across the electrodes. The circuit includes means for synchronizing the ac current to the clock to time the sampling so that the same polarity of signal input is always obtained. Where the known ac current source consists of switching the sense of the electrode connections to a combination of a dc source in series with a known resistor, used for supplying the reference input to the converter, a dc signal input, instead of ac, obtained by including the voltage drop of the switch with the drop across the electrodes in the signal sampled. With this arrangement, higher cell constants can be used to minimize the effect of the voltage drop across the switch.

16 Claims, 4 Drawing Sheets

CONDUCTIVITY MEASURING CIRCUIT

BACKGROUND OF THE INVENTION

In measuring the conductivity of a liquid, such as a solution in a cell having two electrodes, conventional measuring systems apply to the electrodes an ac voltage in order to avoid polarization and related problems during the measurement. As the conductivity of the solution being measured changes, the resistance of the cell, and therefore the voltage drop associated with it, changes. A measure of this cell voltage drop is indicative of the conductivity of the solution. To obtain an indication of the conductivity, however, has in the past necessitated the conversion of the ac to dc before detection, or the use of an ac detection. These requirements have made the measurement of solution conductivity complicated, and the equipment for making such measurements expensive.

It is an object of this invention to provide a simple and inexpensive solution conductivity measuring circuit, preferably one which can be packaged as a small unit; shaped like a pen, for example, for convenient carrying of the unit in ones shirt pocket. It is a further object of this invention to provide such measurements using a dc circuit arrangement utilizing integrated circuit packages in order to make possible the small size required for easy portability.

SUMMARY OF THE INVENTION

There is provided a conductivity measuring circuit for measuring the conductivity of a solution. This circuit includes an analog-to-digital converter for producing a digital output indicative of the analog voltage drop across its signal input terminals. The voltage drop is provided by a pair of electrodes immersed in the solution to be measured and is sampled before each conversion cycle by a capacitor associated with the converter. The sampling is timed by the converter clock in a manner such that the capacitor is always fully charged in the proper polarity at the end of the sampling period. The capacitor then provides the input to be converted by the converter. To produce the voltage drop across the electrodes indicative of conductivity, the electrodes are connected to a source of ac current that is synchronized with the clock of the analog-to-digital converter.

In one form of the invention a pair of current input terminals are provided in conjunction with a switching circuit so as to connect the current input terminals to the electrodes through the switching circuit alternately in one sense and then the other. With the current input terminal connected in series circuit with a known resistance and a source of dc voltage, their is provided the source of known ac current for the electrodes. The current is known because the known resistance is connected across the reference input of the converter so that integration in one phase of the conversion process is in response to the drop across the known resistance. The voltage drop across the electrodes can be connected to the signal input of the converter either directly or through the switch, as by connecting the converter signal input to the current input terminals instead of directly to the electrodes.

BRIEF DESCRIPTION OF THE DRAWINGS

In the drawings, in which like reference characters represent like elements and the pin designations and nomenclature are those of the manufacturers:

FIG. 2a is a circuit diagram of the analog section of a 7126.

FIG. 2b is a circuit diagram of the digital section of a 7126.

DESCRIPTION OF THE PREFERRED EMBODIMENT

Figure 1:
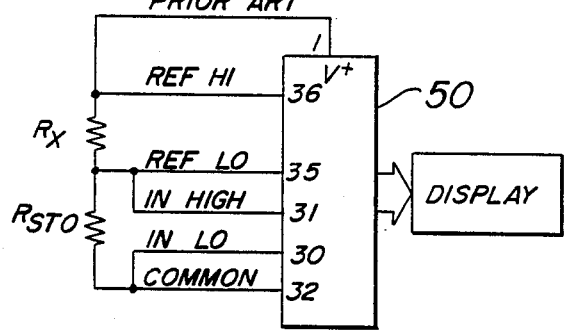
FIG. 1 is a circuit diagram of a prior art ratiometric conductivity measuring circuit for measuring the conductivity of elements, such as a resistance element, which only requires the use of dc. This circuit utilizes a solid state analog-to-digital converter of the 7126 type for converting dc voltage drops to digital outputs for display.

In FIG. 1 there is shown a prior art circuit which can be used to measure the conductivity of an element, such as the unknown resistor $R_x$. This is accomplished by a ratiometric measurement, whereby the unknown resistance is measured with respect to a known standard resistance, $R_{std}$. This method requires no accurately defined reference voltage or current. Instead it uses a common current passing through both a standard and an unknown resistance in order to develop across the unknown, $R_x$, a voltage which can be applied to one differential input of an analog-to-digital converter 50 (shown as a 7126, for example) as the signal or unknown input and another voltage across the standard, $R_{std}$, which can be applied to the other differential input of the converter as the reference or known input. The converter will produce an output to the display which will give a display reading of $(1000)R_{std}/R_x$ in the units of mhos. For resistance measurements, instead of conductivity measurements, it is only necessary to interchange $R_x$ and $R_{std}$. Then the voltage drop across the known resistance will be supplied to the terminals REF HI and REF LO, with the drop across the unknown supplied to the terminals, IN HIGH and IN LO (this being the normal orientation for the terminals, their names are properly descriptive).

As a help in understanding how the ratiometric measurement of FIG. 1 is made by the analog-to-digital converter 50, FIGS. 2a and 2b, which show the converter circuit, are briefly described below. This description shows how the analog and digital sections of a 7126, which is an integrated circuit analog-to-digital converter of the dual slope type, operates to provide the desired measurement of a dc voltage drop.

Figure 2:
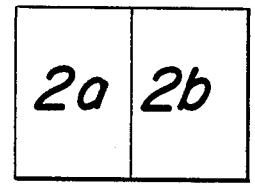
FIG. 2 is a diagram showing how
Figure 2A:
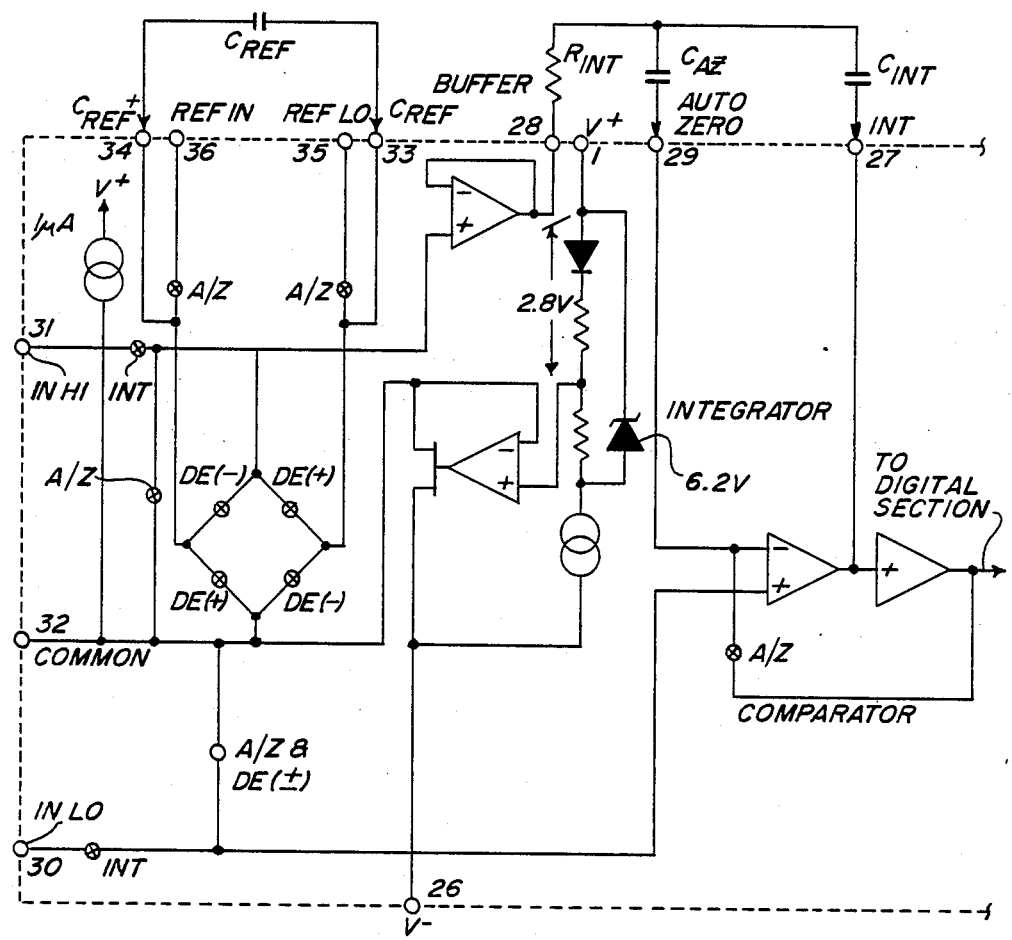
FIGS. 2a and 2b are juxtaposed to produce FIG. 2.

FIG. 2a shows the analog section of a single chip CMOS TSC7126 as manufactured by Teledyne Semiconductor and illustrated on page 7-73 of their Data Acquisition Design Handbook of 1984. This drawing shows the typical elements of a dual-slope integrating analog-to-digital converter having two differential inputs along with the necessary external components which must be added to cause it to operate as desired. For the purposes of this application, the external or auxiliary circuitry of FIGS. 2a and 2b, required to operate the 7126, will be considered a part of the 7126 when it is shown in subsequent drawings. Likewise, reference to an integrated analog-to-digital converter shall be considered to include the necessary external circuitry for operation as a converter unless the external circuitry is specifically described.

As is well known, the conventional dual-slope converter measurement cycle has two distinct phases: the input signal integration and the reference voltage integration (deintegration). The input signal being converted is integrated for a fixed time period. Time is measured by counting clock pulses. An opposite polarity, constant reference voltage is then integrated until the integrator output voltage returns to zero. The reference integration time, as measured by the clock, is then proportional to the input signal.

In addition to the basic signal integrate and deintegrate cycles mentioned above, the design shown in FIG. 2a incorporates an auto-zero cycle. This cycle removes buffer amplifier, intergrator, and comparator offset voltage error terms from the conversion. A true digital zero reading results without external adjusting potentiometers. A complete conversion will then consist of three cycles: an auto-zero, signal integrate and reference integrate (deintegrate) cycle.

During the auto-zero cycle (1000 to 3000 counts, depending on the length of deintegration) the differential input signal is disconnected from the circuit by opening internal analog gates. The internal nodes are shorted to analog common (ground) to establish a zero input condition. Additional analog gates close a feedback loop around the integrator and comparator. This loop permits comparator offset voltage error compensation. The voltage level established on capacitor $C_{az}$ compensates for device offset voltages.

The auto-zero loop is opened and the internal differential inputs connect to $V_{in}+$ and $V_{in}-$. The differential input signal is integrated for a fixed time period (1000 counts). The externally set clock frequency is divided by four before clocking the internal counters. The integration time period is then:

$T_{si}=(4/f_{osc}\times 1000)$ where:

$f_{osc}$ = external clock frequency

The final phase is reference integrate or deintegrate. $V_{in}-$ is internally connected to analog common and $V_{in}+$ is connected across the previously charged reference capacitor $C_{ref}$. Circuitry within the chip ensures that the capacitor will be connected with the correct polarity to cause the integrator output to return to zero. The time required for the output to return to zero is proportional to the input signal and is between 0 and 2000 internal clock periods. The digital reading displayed is $1000(V_{in}/V_{ref})$.

Figure 2B:
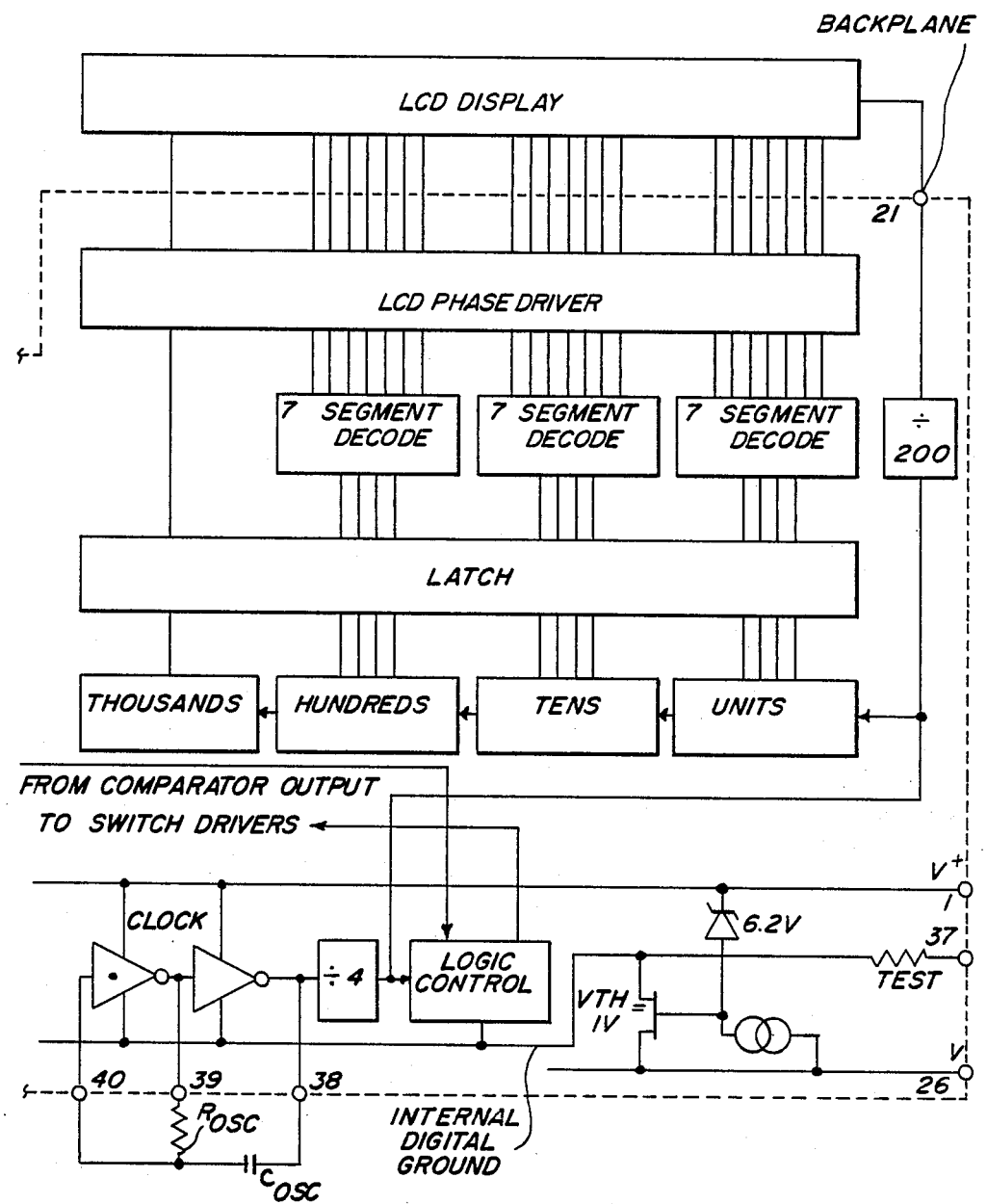

The digital section of the same 7126 integrated package is shown in FIG. 2b. It contains all the segment drivers necessary to drive a 3½ digit liquid crystal display. An LCD backplane driver is included. The backplane frequency is the external clock frequency divided by 800. For three conversions/sec. the backplane frequency is 60 Hz with a 5 volt nominal amplitude. When a segment driver is in phase with the backplane signal the segment is "off". An out of phase segment drive signal causes the segment to be "on" or visible.

The frequency of the clock of the 7126 is determined by the RC network which uses the three pins, 38, 39, and 40. This network includes $R_{osc}$ connected between pins 39 and 40 and $C_{osc}$ connected between pins 38 and 40.

Since it is desired to use a solid state analog-to-digital converter, such as a 7126, to make a small unit for measuring the conductivity of a solution rather than of a resistor, as in FIG. 1, one would expect that it could not be done since it would be necessary to alter the circuit of FIG. 1 so as to apply an ac voltage to the unknown electrode voltage drop while supplying a dc to the known resistance. The use of ac would be expected to require the use of a complex means for detection of the unknown, instead of the 7126, which is known to be a dc device. I have found that this problem can be solved in one way by making the dc current source look like an ac current source to the cell while the cell voltage drop looks like dc to the 7126 analog-to-digital converter. The circuit of FIG. 3 is a circuit diagram of one form of my invention which allows that to be accomplished.

Figure 3:
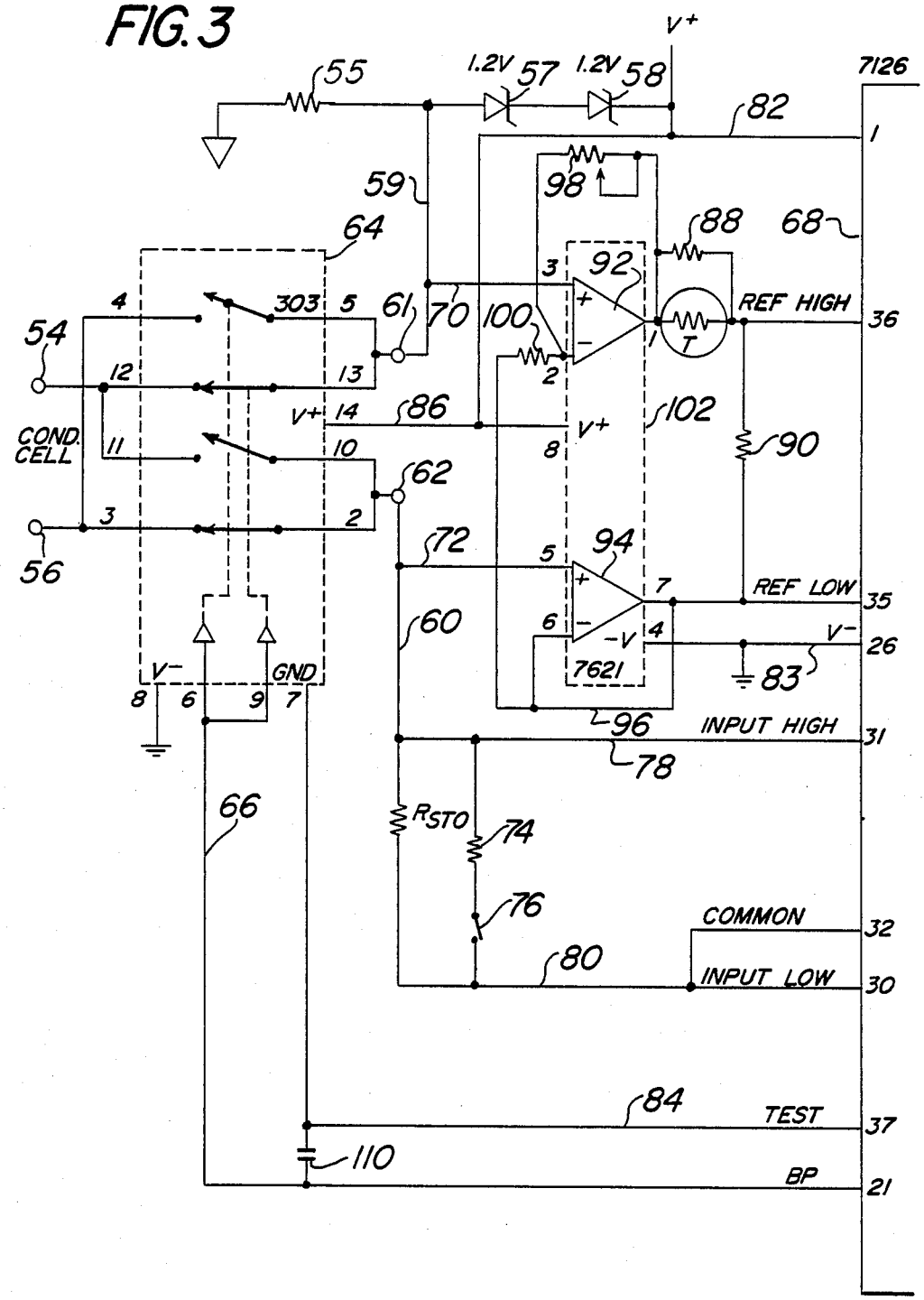
FIG. 3 is a circuit diagram of a conductivity measuring circuit which is one form of the invention.

In FIG. 3 the conductivity of a solution in a conductivity cell (not shown) is measured by connecting the cell across cell input terminals 54 and 56. Using the ratiometric method described in relation to FIG. 1, the voltage across resistor 55, which is slightly less than V+ (by the drop across the two diodes 57 and 58), is connected through a first circuit (leads 59 and 60) across a series circuit including current input terminals 61 and 62 and the known resistance element $R_{std}$. The fact that the current flow will vary with changes in conductivity of the solution in the cell will, of course, be of no importance in this circuit since the current through the cell and $R_{std}$ will always be the same. That current may be considered to be a known dc current since the drop across the known resistance is supplied as a known input to the converter.

The cell input terminals are connected to the current input terminals by a switching circuit which includes switch means 64 for connecting the current input terminals alternately to the cell terminals in one sense, or polarity, and then in the other sense at a rate of actuation sufficient to prevent polarization of the cell by the dc applied to the current input terminals. The switch means 64, as shown in FIG. 3, may be a type 303 switch, such as can be purchased from Harris. This switch is driven by an ac signal on line 66, which is shown as the backplane signal from a 7126 type analog-to-digital converter 68 which may be operating at a frequency of 44 Hz, for example. In one position of the switch, as shown, pins 2 and 3 are connected and pins 12 and 13 are connected so as to connect the cell terminal 54 to current input terminal 61 and cell terminal 56 to current input terminal 62, all of which makes the terminal 54 positive. In the other position of the switch the connections of the cell input terminals to the current input terminals are reversed and the terminal 54 is negative, since it is connected to terminal 62 through the connection of pins 10 and 11 by the switch. Terminal 56 is then positive by way of its connection to terminal 61 through connection of pins 4 and 5 by the switch. Thus, to the cell connected to the cell input terminals it appears that an ac voltage is being used since current flow through the cell is alternately in one direction and then the other.

It also seems to be necessary to make the voltage drop across the cell look like a dc voltage drop to the input terminals of the analog-to-digital converter. I have found one way of doing this is to connect, by a second circuit, the current terminals 61 and 62 and the signal input of the converter 68 so the converter can detect the cell voltage drop. The second circuit in FIG. 3 consists of leads 70 and 72 plus any circuitry interposed in those two leads as they connect to the differential signal input of the converter, pins 35 and 36, so as to detect the cell drop. Those terminals are here identified as REF HIGH and REF LOW. In this arrangement it will be evident that the voltage drop detected by the converter at pins 35 and 36 will not only be the drop across the cell but also will include the drop across the switch 64. There will, therefore, be introduced a certain amount of inaccuracy depending on the resistance of the switch. This inaccuracy can be alleviated somewhat by using a cell with a high cell constant, such as a constant of 10, for example.

As shown in FIG. 3, the standard resistance, $R_{std}$, is arranged to be paralleled by a second standard resistance 74 when switch 76 is closed. The purpose of resistor 76 is to provide a decade change in range for the circuit. As shown, the standard resistance and its parallel resistance 74, when used, is connected as the reference input across the remaining differential input, INPUT HIGH and INPUT LOW (at pins 31 and 30, respectively), of the converter 68 by leads 78 and 80. In this arrangement the common terminal of the converter, pin 32, is made common with the INPUT LOW terminal, 30.

The positive side of the voltage supply is connected to the converter 68, at pin 1, by way of lead 82, and the ground side is connected by lead 83 to pin 26 of the converter.

The ground connection for the switch 64, pin 7, is connected to digital ground for the converter at pin 37, which is labelled TEST, by lead 84. The positive side of the voltage supply to the switch is to pin 14 by way of leads 82 and 86.

Since solution conductivity measurements are always referenced to 25 deg. C., it is necessary to compensate the conductivity measurement for the actual temperature of the solution. In the circuit of FIG. 3 this is accomplished by the use of a thermistor, T, which is placed so that it will be immersed in the solution to be measured. In order that the thermistor can characterize the temperature characteristic of the solution properly, it is shunted by a resistor 88 with the shunt combination place in series with another resistor 90, which is across the reference input terminals of the converter, pins 35 and 36. The resistors 88 and 90 must be selected to carefully match the solution temperature characteristic for conductivity. If the thermistor has a resistance of 10K at 25 deg. C., for example, resistors 88 and 90 can advantageously have values of 41.2K and 5.25K, respectively. With this arrangement the shunt combination of the thermistor and resistor 88 forms a voltage divider with resistor 90 so that only a part of the potential drop across the cell is seen by the reference input of the converter, and that part varies with the temperature of the solution in the cell.

In order to prevent the voltage divider from loading the cell, it is important to make the divider look like a high impedance circuit to the cell. This is done by interposing operational amplifiers in the leads 70 and 72 as part of the temperature compensating network. Thus, lead 70 is connected to the noninverting input of amplifier 92 to produce a potential at its output which is applied to one side of the temperature compensating circuit. Likewise, the lead 72 from current terminal 62 connects to the noninverting input of amplifier 94, which produces at its output the input to the other side of the temperature compensating circuit and the REF LOW input of the converter at pin 35. The negative feedback for amplifier 94 is by way of lead 96 so that the inverting input is connected directly to the amplifier output making the amplifier a follower in that its output signal follows its input signal. For amplifier 92 the negative feedback is by way of variable resistor 98 to the inverting input of the amplifier, which input is also connected to the output of amplifier 94 by way of resistor 100. With this connection, the resistors 98 and 100 form a voltage divider which varies the part of the output of 92 which is fed back to its inverting input in accordance with the setting of resistor 98. The output of amplifier 92 will then be maintained at a level sufficient to keep the input to its inverting input at the same level as the input to the noninverting input, representative of the cell drop. Variable resistor 98, therefore, provides a means for calibrating the circuit. The two amplifiers 92 and 94 can be a package 102, such as a 7621, shown with the dashed lines enclosing the amplifiers. The positive of the voltage supply for the package can be supplied to its pin 8 by lead 86, whereas the ground connection can be supplied by way of lead 83 to pin 4.

It has been found that the use of a make-before-break switch, such as the 303, results in the gerneration of spikes in the reference input. These spikes can create a error in the output of the converter. Such errors can be avoided by adding the capacitor 110 between the backplane lead 66 and the TEST, lead, or digital ground, as shown. This capacitor causes a slight delay in the switching of switch 64 so that the spikes occur after $C_{ref}$ has been disconnected.

Figure 4:
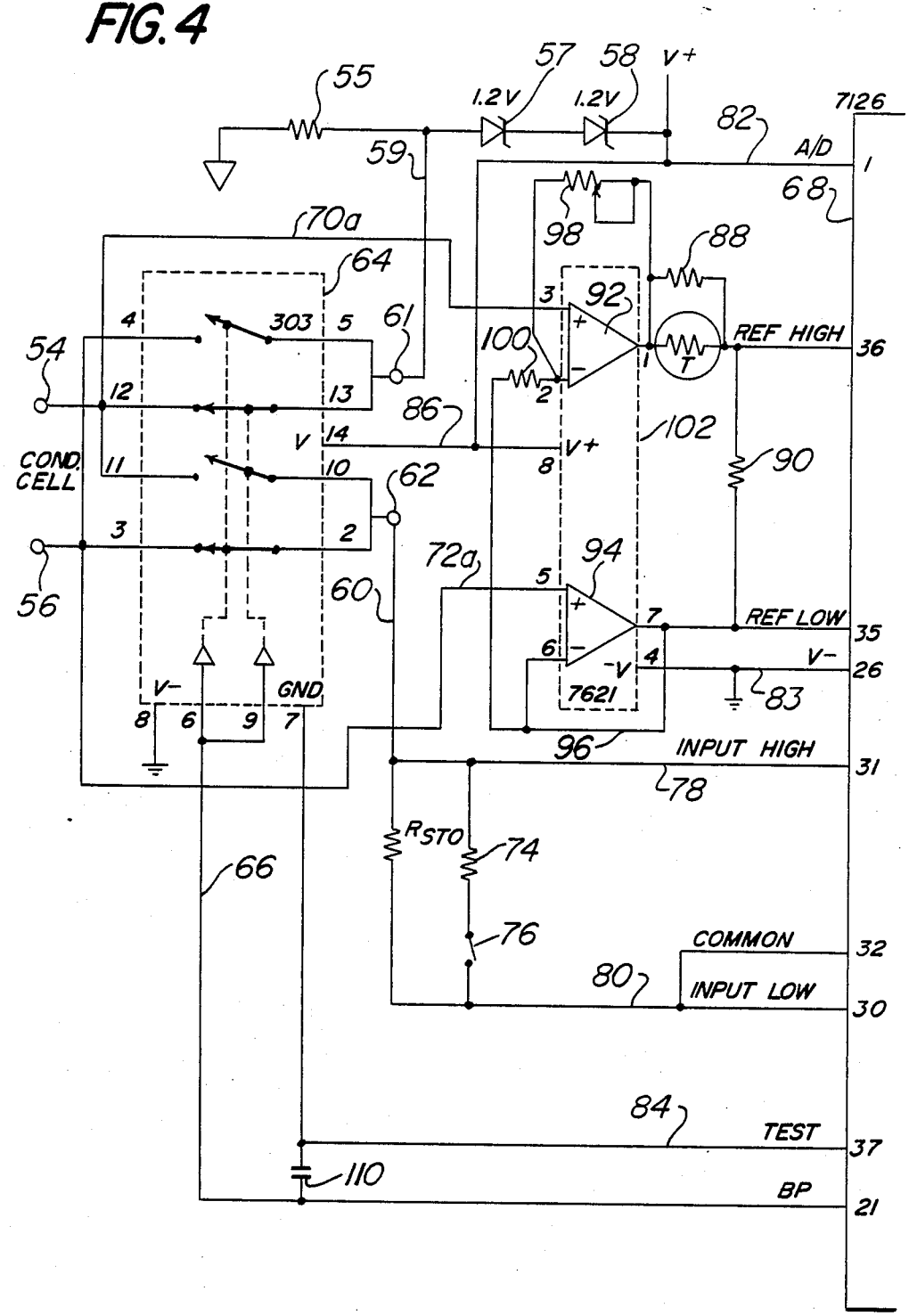
FIG. 4 is a circuit diagram of a conductivity measuring circuit which is another form of the invention.

If it is desired to eliminate the voltage drop due to the resistance of the switch 64 from inclusion with the cell drop in determining the conductivity of the cell, the connections between the converter signal input terminals 35 and 36 and the cell input terminals can be by way of leads 70a and 72a (instead of through the switching element), the temperature compensating network, and the associated amplifiers, as shown in FIG. 4. Thus, FIG. 4 differs from FIG. 3 only in the addition of leads 70a and 72a and the ommission of leads 70 and 72. One cell input terminal 54 is connected by lead 70a to the noninverting input of amplifier 92 and the other cell input terminal 56 is connector by lead 72a to the noninverting input of amplifier 94.

The connection of the cell input terminals directly to the converter presents a problem, however, for converters such as the 7126 are designed for conversion of dc voltages only. I have, however, found that by using the back plane drive signal, from pin 21 of the converter, as the drive for the switch 64, it is possible to detect the voltage drop across the cell even though it is alternating in polarity at a rate determined by the back plane signal. This circuit appears to work because the reference input connects to a capacitor $C_{ref}$(FIG. 2a) to charge that capacitor with the input from the cell during the entire auto-zero portion of the cycle. The charge on the capacitor will switch polarity several times during the complete conversion cycle, however, timing insures that the capacitor will have a positive polarity at the end of its charging cycle because the capacitor is disconnected internally by the 7126 converter on a positive half cycle of the 303 switch. This timing is hardware specific and cannot change. The fact that the switching cycle of switch 64 and the conversion by the analog-to-digital converter are being timed by the same clock makes possible the conversion of a voltage which looks like an ac at the converter input. It is, of course, necessary that the charging of capacitor $C_{ref}$ be carried out for a period long enough to fully charge $C_{ref}$ after the last change in polarity of the ac at the converter input.

With the arrangement of FIG. 4 it is possible to use cell constants that are lower than those needed for the circuit of FIG. 3. The cell constant can be 1, for example, when using the circuit of FIG. 4. Better accuracy and wider ranges for conductivity measurements are other benefits realized by use of the circuit of FIG. 4.

The parameters of the circuits of FIGS. 2, 3 and 4, not previously stated, may advantageously be of the following values:

| component | value |
| --- | --- |
| $C_{ref} =$ | .1 microfarads |
| $C_{int} =$ | .056 microfarads |
| $C_{az} =$ | .15 microfarads |
| $C_{osc} =$ | 56 picofarads |
| 110 = | 1 microfarad |
| $R_{osc} =$ | 180K |
| $R_{int} =$ | 1 M |
| $R_{std} =$ | 1 M |
| 74 = | 111K |
| 55 = | 100K |
| 98 = | 10K |
| 100 = | 3.01K |

As has been indicated solid state analog-to-digital converters other than the 7126 can be used. It is only necessary that they have differential inputs and a sampling capacitor associated with the reference input. Likewise, switching elements other than the 303 can be used and the operational amplifiers can be provided without limiting one's choice to the 7621 mentioned. It will also be evident to those of ordinary skill in this art that ac current sources may be obtained by means other than by switching a dc current source, as illustrated in this description. It will further be evident that resistance measurements can be made instead of conductivity by merely reversing the input connections as pointed out in connection with FIG. 1, as long as the capacitor sampling is done on the unknown input when ac is being sampled. Alternatively, of course, the output can be inverted. Such variations are meant to be within the scope of equivalents covered by the claims.

For the purposes of the claims, the unknown input signal to the analog-to-digital converter will be referred to as the signal input and will be referred to as being connected to terminals identified as signal input terminals, regardless of the nomenclature used by the manufacturers in connection with those terminals on integrated circuit packages. The manufacturers nomenclature is shown in the drawings. Similarly, the known input to the converter will be referred to as the reference input and the terminals to which it is connected will be referred to as the reference input terminals, regardless of the manufacturers nomenclature.

What is claimed is:

1. A conductivity measuring circuit for measuring the conductivity of a solution in a conductivity cell, comprising:

an analog-to-digital converter having signal input terminals and digital output terminals, said converter being operable to produce a digital output at said output terminals indicative of the voltage drop across its input terminals;

a pair of current input terminals;

a source of known dc current;

first circuit means connecting said current input terminals to said source of known dc current;

a pair of cell input terminals;

cell switching means for connecting said current input terminals alternately to said cell terminals in one sense and then the other at a rate of actuation sufficient to prevent polarization of the cell while causing said known dc current to flow through said cell; and second circuit means for connecting the voltage drop across said cell input terminals to said converter signal input terminals for conversion of the voltage drop to a digital output indicative of the magnitude of the conductivity of the solution in said cell.

2. A measuring circuit, as set forth in claim 1, in which said second circuit means connects the voltage drop across said cell input terminals to said converter signal input terminals by connecting said converter signal input terminals to said current input terminals whereby connection of said converter signal input to said cell input terminals is by way of said switching means.

3. A measuring circuit, as set forth in claim 1, in which said second circuit means connects the voltage drop across said cell input terminals to said converter signal input terminals by connecting said converter signal input terminals to said cell terminals in avoidance of said switch means.

4. A measuring circuit, as set forth in claim 1 or 3, in which said analog-to-digital converter includes capacitor means for sampling the voltage drop across the converter input terminals and for supplying the sampled value for conversion.

5. A measuring circuit, as set forth in claims 1, 2, or 3, in which said analog-to-digital converter is an integrated circuit device.

6. A measuring circuit, as set forth in claims 1, 2, or 3, in which said second circuit includes:

two leads connecting said voltage drop across said cell input terminals to said converter signal input terminals; and a temperature compensating circuit inserted in said two leads, said compensating circuit having, a first operational amplifier having its input connected to one of said cell input terminals, a second operational amplifier having its input connected to the other of said cell input terminals, a thermistor arranged to be immersed in said solution being measured, a first resistor shunting said thermistor, said shunt combination being connected in series between the output of one of the first and second amplifiers and a first of said converter signal input terminals to form a junction therewith, a second resistor connecting the junction between said thermistor and said first converter signal input terminal to a second of said signal input terminals, and means for connecting the output of the other of said first and second amplifiers to said second signal input terminal so that the voltage drop appearing between the outputs of said amplifiers is divided in a manner dependent on the temperature detected by said thermistor to compensate the voltage drop across said cell for the temperature of the solution being measured.

7. A measuring circuit, as set forth in claims 1 or 3, in which said analog-to-digital converter includes:
capacitor means for sampling the voltage drop across the converter signal input terminals; and
said cell switching means has a rate of actuation which is timed so that said sampling is always carried out for at least a full half cycle of said switching means and so that said sampling always ends at the end of a half cycle of said switching means.

8. A measuring circuit, as set forth in claims 1, 2, or 3, in which
the signal input terminals of said converter are a differential input;
the source of dc current includes, in series,
a source of dc potential and
a known resistance; and
said analog-to-digital converter includes a pair of differential reference input terminals connected to receive as a differential input the voltage drop across said known resistance, whereby said last named voltage drop provides an input to said converter indicative of the magnitude of said dc current.

9. A conductivity measuring circuit for providing a compact portable instrument for measuring the conductivity of a solution, comprising:
a pair of electrode input terminals for connecting to electrodes forming a conductivity cell;
voltage input terminals for connection to a source of known dc voltage;
a known resistance;
a pair of current input terminals;
first circuit means connecting said dc voltage input terminals in series with said current input terminals and said known resistance so as to produce a known dc current source across said current terminals;
an analog-to-digital converter of the dual slope type having an input signal integration phase and a reference voltage integration phase, said converter being in the form of an integrated package and having associated circuitry which includes
a clock for timing the conversions of said converter,
a reference capacitor,
a pair of differential converter signal input terminals for receiving a voltage drop as the input signal for one of said integration phases of said converter, and
a pair of differential converter reference input terminals for receiving another voltage drop as the input signal for the other of said integration phases of said converter;
first circuit means connecting said dc voltage input terminals in series with said current input terminals and said known resistance and for connecting said known resistance across said reference input terminals so as to produce a known dc current source across said current terminals;
switching means for connecting said current input terminals alternately to said electrode input terminals in one sense and then the other at a rate synchronous with the operation of said converter and sufficient to prevent polarization of the electrodes; and
second circuit means for connecting said electrodes to said converter signal input terminals for conversion of the voltage drop across said electrodes to a digital output indicative of the magnitude of the conductivity of said solution in said cell.

10. A conductivity measuring circuit, as set forth in claim 9, in which
said second circuit means comprises two leads which connect said electrode input terminals to the differential converter signal input terminals, said leads having interposed therein a temperature compensating means comprising:
a first operational amplifier receiving input from one of the electrode input terminals;
a second operational amplifier receiving input from the other of said electrode input terminals;
a thermistor arranged to be immersed in said solution;
a first resistor shunting said thermistor, said shunt combination being connected in series between the output of the first amplifier and a first of said converter signal input terminals; and
a second resistor connecting the junction between said thermistor and said first signal input terminal to the output of the second amplifier and to a second of said signal input terminals so that the voltage drop appearing between the outputs of said amplifiers is divided in a manner dependent on the temperature detected by said thermistor to compensate the signal input to said converter signal input terminals for the temperature of the solution being measured.

11. A conductivity measuring circuit, as set forth in claim 10, in which:
said first operational amplifier has its input from said one electrode input terminals connected to its noninverting input;
said second operational amplifier has its input from said other electrode input terminal connected to its noninverting input; and
said first operational amplifier has its inverting input connected to the output of said second amplifier through a third resistor and its output connected to its inverting input through a variable resistor so that changes in the setting of said variable resistor may be used to calibrate said measuring circuit.

12. In a ratiometric conductivity measuring circuit for measuring the conductivity of a solution in a conductivity cell wherein the circuit has an analog-to-digital converter of the dual slope type which includes an integrating circuit, a clock circuit for timing the periods of integration carried out by the integrating circuit in sequential conversion cycles, first and second pairs of voltage input terminals, first switch means for connecting said integrating circuit to receive a first input from said first pair of voltage input terminals to integrate the voltage received at those terminals for a fixed period of each sequential cycle as timed by said clock circuit to produce a voltage output from said integrating circuit ramping from a reference value for said fixed period as a first part of the conversion cycle, and for subsequently switching said integrating circuit to integrate a second voltage sampled over a short period from the voltage appearing at second terminals as a second part of said conversion cycle to produce a voltage output from said integrating circuit which ramps back toward said reference value for a variable period sufficient to bring the output of the integrating circuit back to said reference value so that said converter produces a digital output proportional to the second voltage, the combination comprising:

a pair of current input terminals;

cell terminals for connection to a conductivity cell immersed in the solution whose conductivity is to be measured;

a known standard resistance;

circuit means forming a series circuit including said current input terminals and said standard resistance in series with a voltage source and for connecting said cell input terminals to said second voltage input terminals and said standard resistance across said first voltage input terminals; and second switch means for connecting said current input terminals alternately to said cell terminals in one sense and then the other at a rate determined by said clock circuit and sufficient to prevent polarization of said cell, said switch means being driven in synchronism with said clock, whereby said cell receives an ac voltage across its terminals and said second voltage input terminals of said converter receive a voltage drop for conversion to a measurement of the conductivity of said solution in digital form.

13. A measuring circuit, as set forth in claim 12, in which said circuit means connects said cell input terminals to said second voltage input terminals by way of said second switch means and said current input terminals.

14. A measuring circuit, as set forth in claim 12, in which said circuit means connects said cell input terminals to said second voltage input terminals directly in avoidance of said second switch means.

15. A circuit for measuring the conductivity of a solution, comprising:

electrode terminal means for receiving a pair of electrodes immersed in said solution;

means connecting a source of known ac current across said electrode terminal means;

a dual slope analog-to-digital converter of the integrated circuit type having a conversion cycle including a signal input integration phase and a reference integration phase, said converter including signal input terminals for receiving the signal to be converted, a clock for controlling said phases of converter operation, and a capacitor for sampling the signal input in synchronism with said clock;

means for connecting said signal input terminals to receive as the input for conversion the voltage drop across said electrode terminal means due to said ac current; and means for synchronizing said ac current to said clock.

16. A circuit for measuring the conductivity of a solution, as set forth in claim 15, in which:

said ac current source includes a dc voltage source in series with a known resistance and switch means for connecting said series circuit to said electrode terminal means alternately in one sense and then the other with the voltage drop across said resistance connected as an input to said converter for supplying a voltage for integration in one of said phases; and said means for synchronizing said ac current to said clock includes means connecting said switch means to said clock so that its switching operations are timed by said clock.

* * * * *